(12) United States Patent
Zhang et al.

(10) Patent No.: US 6,572,813 B1
(45) Date of Patent: Jun. 3, 2003

(54) BALLOON FORMING PROCESS

(75) Inventors: Michael Y. Zhang, San Diego, CA (US); Kerry J. Williams, Temecula, CA (US); Johann J. Skinner, Cupertino, CA (US); Chicheng Wang, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/483,390

(22) Filed: Jan. 13, 2000

(51) Int. Cl.[7] .............................................. B29C 49/64
(52) U.S. Cl. ..................... 264/519; 264/535; 264/903; 264/904
(58) Field of Search ................................ 264/523, 903, 264/904, 519, 535

(56) References Cited

U.S. PATENT DOCUMENTS

| | | | |
|---|---|---|---|
| 5,017,325 A | | 5/1991 | Jackowski et al. .......... 264/521 |
| 5,304,340 A | * | 4/1994 | Downey ...................... 264/521 |
| 5,500,180 A | | 3/1996 | Anderson et al. ............ 264/532 |
| 5,891,386 A | * | 4/1999 | Deitermann et al. ......... 264/523 |

* cited by examiner

*Primary Examiner*—Suzanne E. McDowell
(74) *Attorney, Agent, or Firm*—Fulwider Patton Lee & Utecht, LLP

(57) ABSTRACT

The present invention is directed to apparatus and method for forming balloons with improved dimensional stability and balloons formed by the same. The method of the present invention provides for a very accurate control of the temperature profile of the balloon material during its making. The attributes of the balloon can be affected by how the balloon is treated during the blowing stage and after the initial blowing, i.e., heat-setting. Using the present method, the balloon will form more uniformly and evenly (e.g., wall thickness and outer diameter of the balloon). The present method significantly increases the dimensional stability of the balloon which provides a balloon that is more predictable, in use. The present heat-set process also provides the means for the working length to be located more accurately on dilation catheters and stent delivery systems.

24 Claims, 5 Drawing Sheets

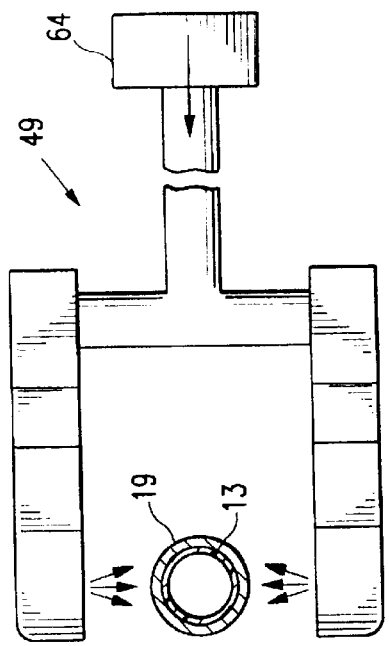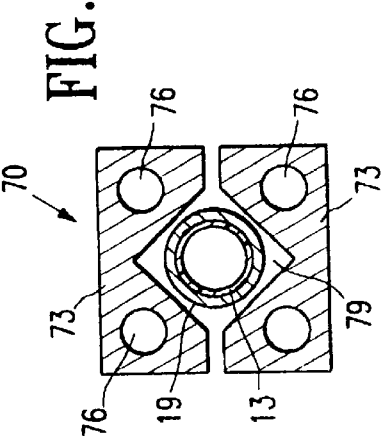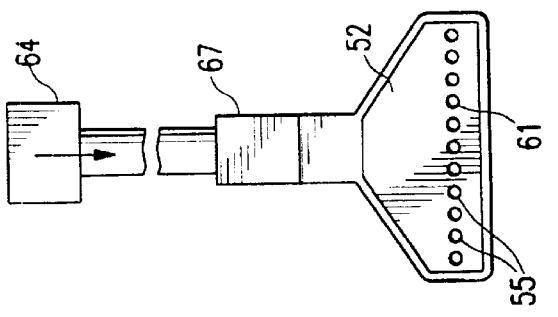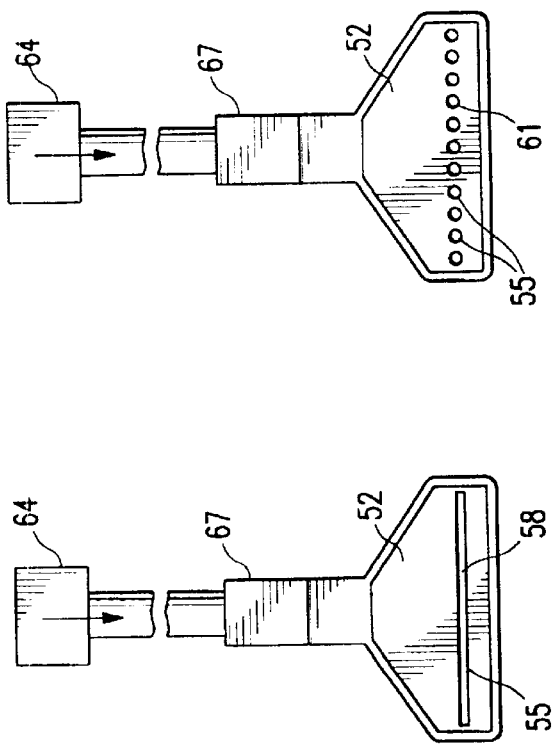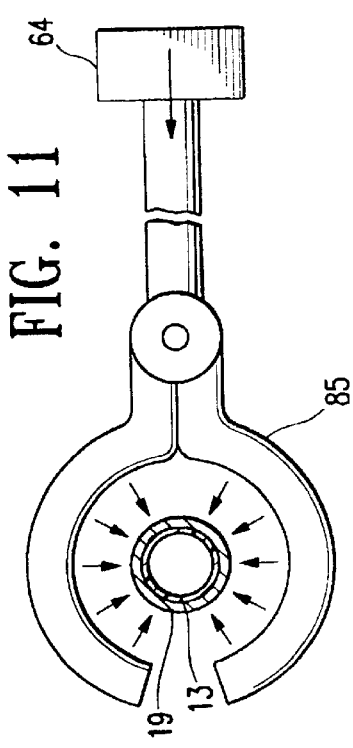

BALLOON FORMING PROCESS

FIELD OF INVENTION

The invention relates to the field of intravascular balloons, and more particularly to method and apparatus for forming balloons.

BACKGROUND OF THE INVENTION

In percutaneous transluminal coronary angioplasty (PTCA) procedures a guiding catheter is advanced until the, distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter, having, an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method, of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. Thus, stents are used to open a stenosed vessel, and strengthen the dilated area by remaining inside the vessel.

In either procedure, substantial, uncontrolled or unpredictable expansion of the balloon against the vessel wall can cause trauma to the vessel wall. For example, although stents have been used effectively for some time, the effectiveness of a stent can be diminished if it is not properly implanted within the vessel. Additionally, the final location of the implanted stent in the body lumen may be beyond the physician's control where longitudinal growth of the stent deploying balloon causes the stent's position on the balloon to shift during deployment. As the balloon's axial length grows during inflation, the stent may shift position along the length of the balloon, and the stent may be implanted upstream or downstream of the desired location in the body lumen. Thus, balloons which have a large amount of longitudinal growth during inflation can frequently provide inadequate control over the location of the implanted stent. Thus, it is important for the balloon to exhibit dimensional stability.

Therefore, what has been needed is an improved method for forming catheter balloons. The present invention satisfies these and other needs.

SUMMARY OF THE INVENTION

The present invention is directed to an apparatus and method for forming balloons with improved dimensional stability and balloons formed by the same.

The method of the present invention provides for a very accurate control of the temperature profile of the balloon material during its making. The attributes of the balloon can be affected by how the balloon is treated during the blowing stage and after the initial blowing, i.e., heat-setting. Using the present method, the balloon will form more uniformly and evenly (e.g., wall thickness and outer diameter of the balloon). The present method significantly increases the dimensional stability of the balloon which provides a balloon that is more predictable in use. The present heat-set process also provides the means for the working length to be located more accurately on dilation catheters and stent delivery systems.

In one embodiment, the method for forming the balloon comprises disposing a polymeric tubular product having an effective length with first and second ends within a mold. The interior of the tubular product is then pressurized. At least a portion of the tubular product is heated to a first elevated temperature for a first predetermined period of time to form the tubular product into a balloon. Preferably, the temperature of the tubular product is maintained to a minimal temperature differential from the first temperature. The tubular product is heated to a second elevated temperature for a second predetermined period of time to heat set the formed balloon. The tubular product (i.e. formed balloon) is then cooled down to substantially ambient temperature and may be subsequently removed. In an embodiment, the temperature differential is less than about 100° C., preferably, less than about 50° C., and more preferably, less than about 20° C. In one embodiment, the first elevated temperature is greater than the glass transition temperature of the polymeric material forming the tubular product, preferably, by at least 10° C., more preferably, by at least 20° C., and most preferably, by at least 40° C. Preferably, the first elevated temperature is less than the melting temperature of the polymeric material forming the tubular product. The second elevated temperature may be equal or greater than the first elevated temperature, and is preferably sufficiently high to thermoset the polymeric material forming the tubular product.

In one embodiment, the tubular product is heated uniformly between the first and second ends to the second elevated temperature for a predetermined period of time to heat set the formed balloon. Preferably, the temperature difference between the first and second ends is less than about 30° C., more preferably, less than 15° C., and most preferably, less than 10° C.

In a preferred embodiment, the tubular product is heated to the first elevated temperature with a first heating member, and to the second elevated temperature with a second heating member. The first heating member may apply the heat as it traverses along the length of the mold. Alternatively, the first heating member has an effective length which is at least substantially the same as the effective length of the tubular product. In this embodiment, the first heating member may then apply the heat to the mold simultaneously across the effective length of the tubular product.

In one embodiment, the second heating member applies heat to the tubular product as it traverses from one end of the tubular product to the other end. Alternatively, the second heating member may apply the heat to the tubular product simultaneously across the effective length of the tubular product.

In another embodiment, the first and second heating members are integral with one another. Alternatively, the first heating member and the second heating member may be on different heating heads. The second heating member may apply the heat to the mold as it traverses along the length of the mold or it may apply the heat simultaneously across the effective length of the mold, and thus, the tubular product.

Balloons formed from the process of the present invention, preferably, have either or both a reduced radial shrinkage and reduced axial growth. Such reduction, being in radial shrinkage or axial growth, preferably, is less than about 10%, more preferably, less than about 6%, and most preferably, less than about 4%.

BRIEF DESCRIPTION OF THE DRAWINGS

FIG. 8 is a bottom view of the apparatus in FIG. 6 taken along lines 8.

FIG. 9 is an alternate embodiment of another heating element.

FIG. 10 is an alternate embodiment of another heating element having heating cartridges.

FIG. 11 is an alternate embodiment of another heating element having a heating head configured in a "C" shape.

DETAILED DESCRIPTION OF THE INVENTION

Figure 1:
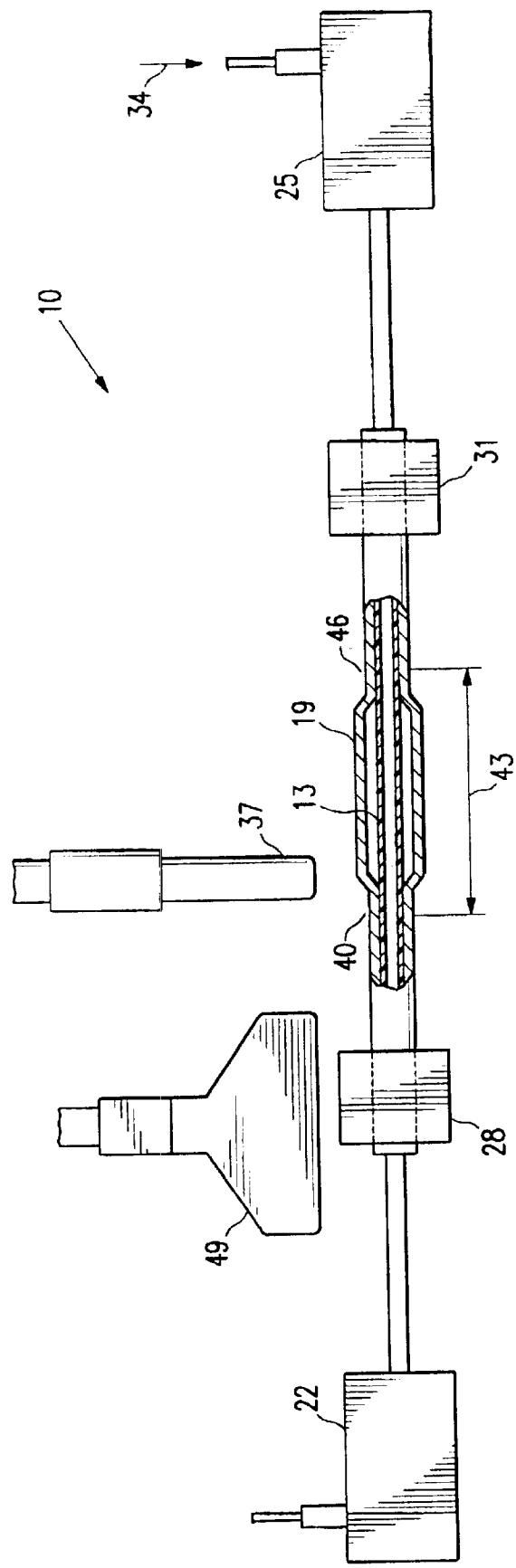
FIG. 1 is a top elevational view, partially cut away, of a balloon forming apparatus.
Figure 2:
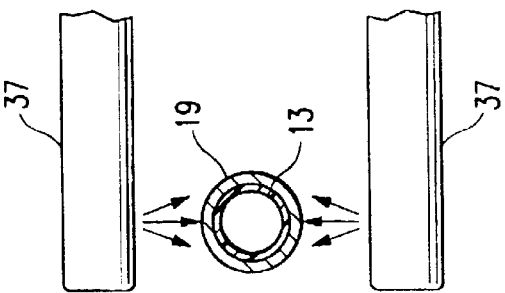
FIG. 2 is a partial top elevational view of the apparatus of FIG. 1 showing a first heating element.
Figure 3:
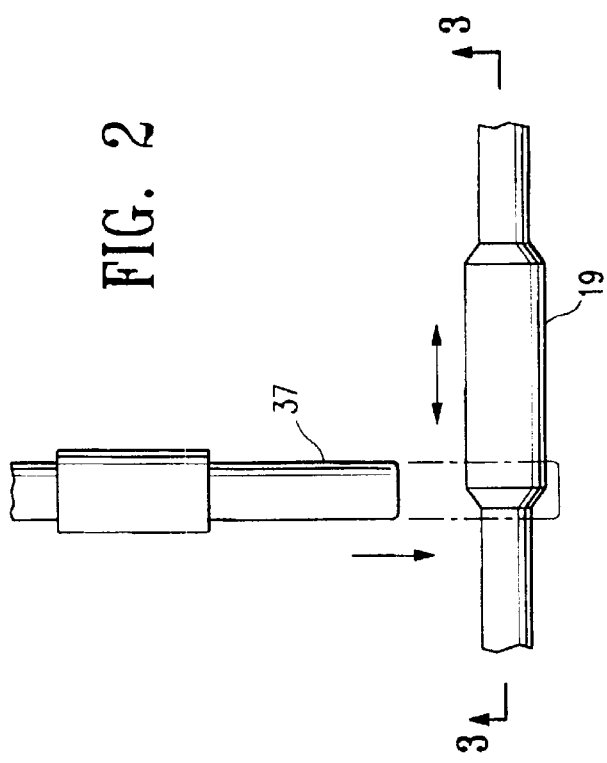
FIG. 3 is a front, partially cut away, elevational view of the apparatus of FIG. 2 taken along lines 3.
Figure 4:
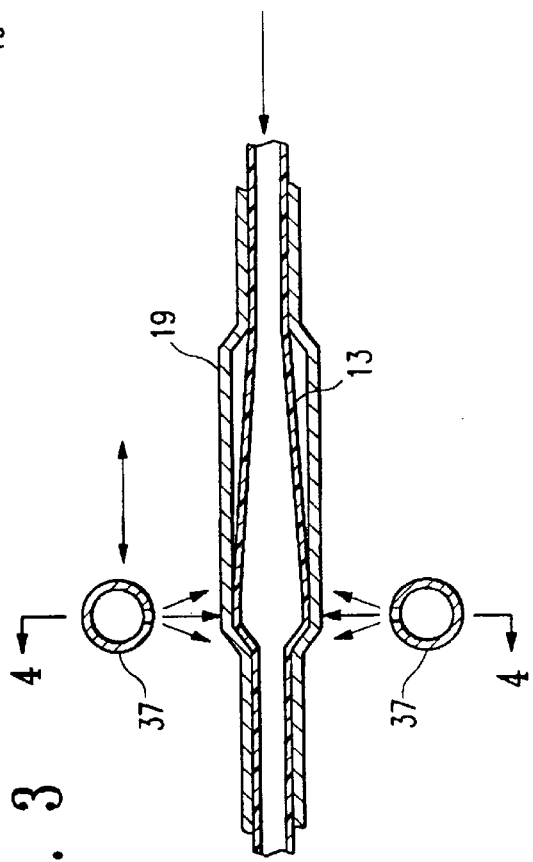
FIG. 4 is a cross sectional view of the apparatus of FIG. 3 taken along lines 4.

The invention relates to a method of making a balloon and apparatus for carrying out the same. The method generally comprises extruding a polymeric tubular product having a first outer diameter. The tubular product is then radially expanded and, preferably axially drawn, to a second outer diameter by heating at least a portion of the tubular product to a first elevated temperature while subjecting the interior of the tubular product to an expansion pressure. While still under pressure, the expanded tubular product is heated to a second elevated temperature. Preferably, the first elevated temperature is greater than the glass transition temperature of the polymeric material forming the tubular product. Preferably, the first elevated temperature is at least 10° C., more preferably at least 20° C., and most preferably at least 40° C., greater than the glass transition temperature of the polymeric material forming the tubular product. The second elevated temperature is sufficiently high to thermoset the polymeric material forming the tubular product. The second elevated temperature may be less, equal or greater than the first elevated temperature. Preferably, the second elevated temperature is equal to or greater than the first elevated temperature.

The transformation of the tubular product into the balloon is performed in a mold having a longitudinal dimension including an effective length with first and second ends, the mold's effective length and the ends substantially corresponding to an effective length and first and second ends of the tubular product which in turns corresponds to the resulting balloon's longitudinal dimension; and a radial dimension suitable for forming the desired size balloon.

Preferably, the temperature of the tubular product along its effective length is maintained to a minimal temperature differential from the first temperature. Preferably, the temperature differential is less than about 100° C.; more preferably, less than about 50° C.; and most preferably, less than about 20° C. It should be noted, that when referring to the temperature of the tubular product, such temperature may be measured directly, or indirectly by correlation, as for example, when measuring the temperature of the heat source or the in mold temperature.

Preferably, the second elevated temperature is uniformly applied to the effective length of the tubular product. Preferably, the tubular product's temperature difference between the first and second ends is less than about 30° C.; more preferably, less than about 15° C.; and most preferably, less than about 10° C.

The expanded, heat-treated tubular product is then cooled to form a balloon.

For example, the formed balloon has a minimal radial shrinkage (for example, as measured by the % change in the outer diameter of the working length of an inflated balloon as part of a catheter system versus as formed after the present process), and minimal axial growth (for example, as measured by the % change in the axial dimension of an inflated balloon as part of a catheter system versus as formed after the present process). Preferably, balloons formed as a result of the present process will exhibit a % shrinkage less than about 10%, more preferably, less than about 6%, and most preferably, less than about 4%. The balloons made according to the present method, may additionally have reduced axial growth of less than about 10%, more preferably, less than about 6%, and most preferably, less than about 4%, as for example when balloons formed from polyurethane.

The balloon is typically formed within a mold having dimensions close to the dimensions of the desired balloon. The blow up ratio, i.e., the balloon outer diameter divided by the balloon tubing inner diameter, is typically about 5.0 to about 8.0, and preferably about 7.0 to about 8.0.

In a presently preferred embodiment, to heat the tubular product to the first elevated temperature during the radial expansion, a first heating member such as a heat nozzle is displaced along a length of the tubular product within the mold, to thereby apply heat to portions of the tubular product adjacent to the first heating member. The expanded tubular product is then heat treated at a second elevated temperature. The heat treatment at the second elevated temperature may be achieved by the first heating member or a second heating member. In either way, the heating member for applying the heat treatment at the second elevated temperature, preferably, applies the heat in such manner as to sufficiently provide a uniform temperature profile across at least substantially the entire length of the mold corresponding to the balloon member (i.e., the effective length). The balloon is then cooled within the mold under pressure.

By way of example, when using a polyurethane tubular product, the first elevated temperature is reached by heating the mold to about 80° C. to about 120° C., and preferably about 95° C. to about 105° C.; and the second elevated temperature is reached by heating the mold to about 100° C. to about 160° C., and preferably about 110° C. to about 140° C. In a presently preferred embodiment, regardless of the material of choice for the tubular product, the second temperature is greater than the first temperature. By way of example, when using a polyurethane tubular product, the second temperature is typically no more than about 10° C. to about 50° C., preferably no more than about 10° C. to about 20° C., greater than the first temperature.

FIGS. 1 through 7, illustrate features of a balloon forming apparatus 10 for transforming a tubular product 13 into a balloon 16 (FIG. 6) for medical devices according to the present invention. The apparatus 10 achieves longitudinal stretching, biaxial orientation, heating, and cooling, in addition to means for monitoring radial expansion or biaxial orientation through suitable means such as hard circuitry, a microprocessor, or other computerized controlling arrangements. For simplicity, many of the details of such apparatus which are commonly known and used in the art are not illustrated. The tubular product 13 is disposed within a mold 19 by inserting the distal and proximal ends of the tubular product 13 through the mold 19 and into corresponding distal and proximal collets, 22 and 25. The mold 19 is then closed and held in place. The tubular product 13 is then subjected to axial tension and pressurized air as is commonly practiced in the art.

To blow the balloon (FIGS. 2 through 4), the interior of the tubular product 13 is pressurized at the desired pressure and a first heating member 37 providing heat at a first elevated temperature is moved from a first position substantially radial to a distal end 40 of an effective length 43 of the mold 19 (i.e., what will be a distal shaft of the balloon 16), over the working length 43, to a second position, substantially radial to a proximal end 46 of the effective length 43 of the mold 19 (i.e., what will be a proximal shaft of the balloon 16). During the movement of the first heating member 37, the tubular product 13 is also being subjected to radial expansion, preferably, also axial stretching. At this time, the tubular product 19 is blown up and formed to substantially its ultimate shape. The blow cycle may include one or more passes of the first heating member 37 along the effective length 43 of the mold 19. Alternatively, as the first heating member 37 traverses along the effective length 43 of the mold, the second heating member 49 may also traverse along this length following the first heating member.

Figure 5:
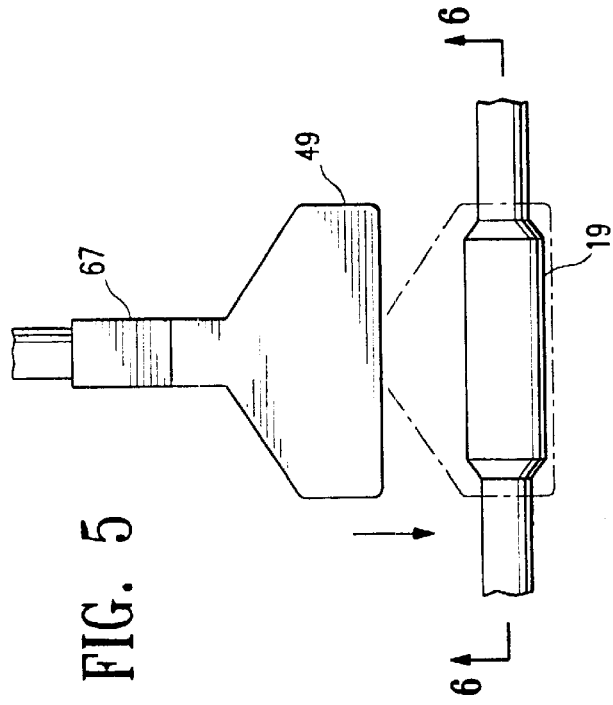
FIG. 5 is a partial top elevational view of the apparatus of FIG. 1 showing a second heating element.
Figure 7:
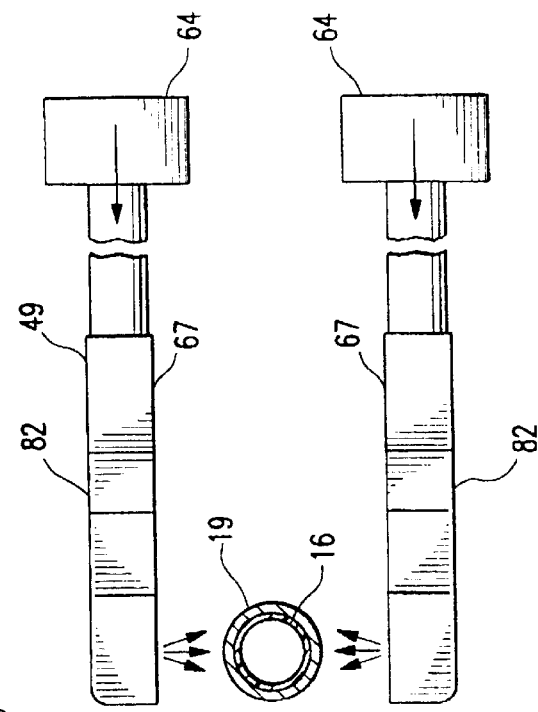
FIG. 7 is a cross sectional view of the apparatus of FIG. 6 taken along lines 7.
Figure 6:
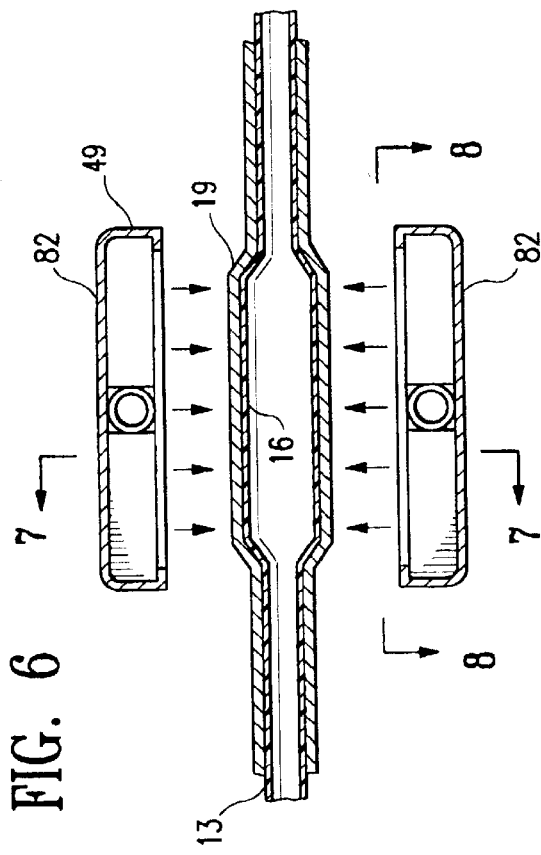
FIG. 6 is a front, partially cut away, view of the apparatus of FIG. 5 taken along lines 6.

After the completion of the blowing cycle (may include one or more passes of the first heating member), the tubular product 13 is then subjected to a second elevated temperature as a second heating member 49 applies heat to the tubular product 13 through the mold 19 (FIGS. 5 through 7). Preferably, the second heating member 49 is of such longitudinal dimension and design so as to apply heat to substantially the entire effective length 43 of the mold 19 at the same time. In other words, preferably, the second heating member 49 is long enough to provide a uniform temperature profile across substantially the entire length of the mold 19, and in effect substantially the entire effective length 43 of the tubular product 13 corresponding to the balloon 16 within the mold 19.

Now referring to FIGS. 8A, 8B, the second heating member 49 includes a heating head 52 having one or more heating nozzles 55. The heating head 52 may have one large nozzle such as slot 58 (FIG. 8A) or a multiple of smaller nozzles such as 61 (FIG. 8B). The heating nozzles 55, may have any shape and number as may be required to heat the mold in the uniform manner desired. The heating nozzles 55 as shown in FIGS. 7, 8A, 8B, 9 and 10 are fluidically connected to a source of hot air 64. The air source 64 may be heated in connecting bodies 67 before exiting the heating nozzles 55.

FIG. 10 illustrates features of an alternate embodiment of a second heating member 70. In this embodiment, the second heating member 70 includes one or more heating heads 73 formed of conductive material such as stainless steel and further includes cartridge heaters 76. To apply heat to the mold 19, the heating cartridges 76 heat the heating head 73. The heating head 73 is brought into physical contact with the mold 19 and the mold 19 is heated by conduction. At points such as 79 where the heating head 73 is not in physical contact with the mold 19, the mold 19 may be heated as heat radiates from the heating head 73 through air and to the mold 19.

In order to uniformly heat the mold 19 from all directions, the second heating member 49, may include one or more individual heating members such as 82, each possibly having a separate heat source (e.g. air) which can heat the mold 19 from two opposite sides, as shown in FIG. 7. Alternatively, the second heating member 49, may be one such as that illustrated in FIGS. 9 and 11, where the heating head 85 is formed in a semi-circular shape or "C" shaped and receiving its heat from a single source. It should be appreciated that the same configuration may also be used for the first heating member 37.

Figure 12:
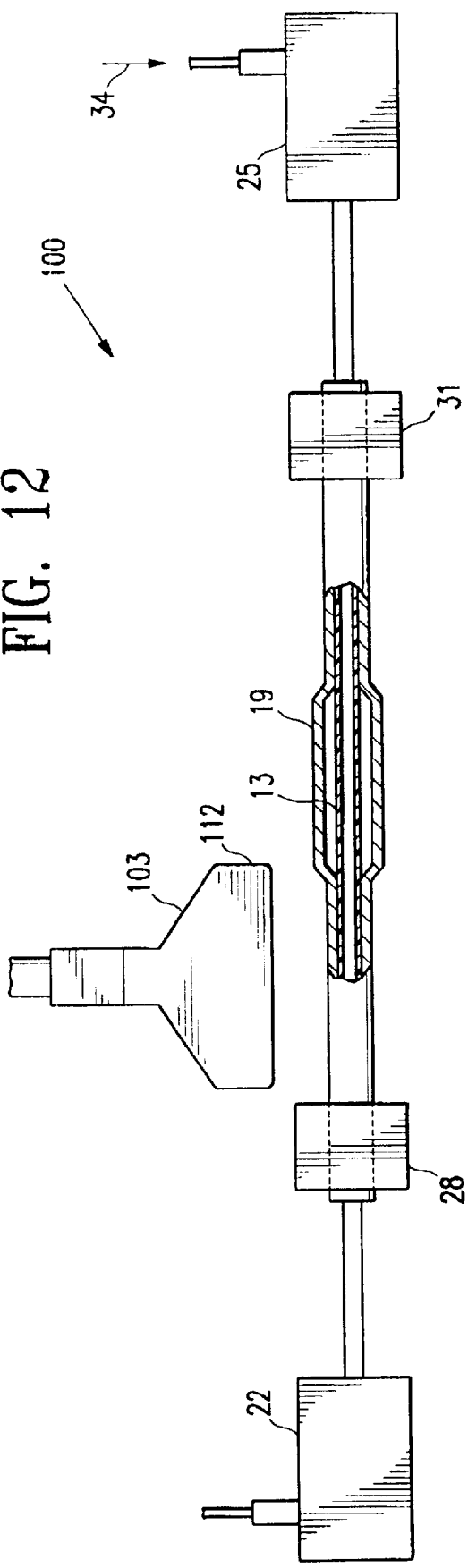
FIG. 12 is a side elevational view, partially cut away, of an alternate embodiment of the balloon forming apparatus of FIG. 1.
Figure 13:
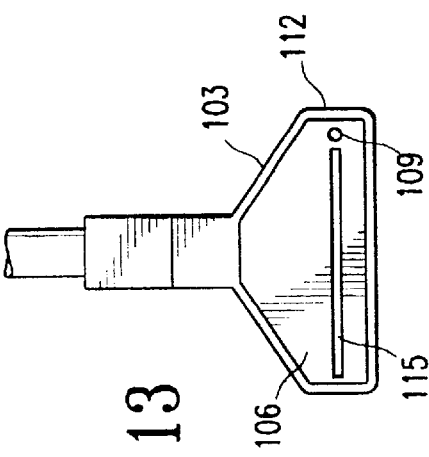
FIG. 13 is an alternate embodiment of an integral heating element.

Now referring to FIG. 12, wherein like references refer to like members, apparatus 100 includes a single integral heating member 103 for both the blowing and heat setting of the tubular product 13 as it is formed into balloon 16. In this embodiment, the integral heating member 103 includes a single heating head 106 with one or more leading nozzles 109 (one as is shown in FIGS. 12, and 13) for heating the tubular product 13 during the blowing stage. As a leading edge 112 of the integral heating member 103 moves from the first position to the second position, the tubular product 13 is blown as described in reference to FIG. 1. When the one or more leading nozzles 109 reach the second position, one or more trailing nozzles 115 apply heat to the mold 19 to heat set the balloon 16. The integral heating member 103 may be formed from multiple single heating heads 106 (as shown in FIG. 13) or multiple heads configured to correspond to the leading nozzle 109 and the trailing nozzle 115 separately.

This embodiment, enables the blowing of the tubular product 13 in a number of desirable fashions. For example, during the blowing stage of the tubular product 13, the integral heating member 103 may be displaced along the effective length 43 of the mold 19 as it traverses from one end to the other. Alternatively, a heating member such as that of FIGS. 8A or 8B may be brought into position (as that illustrated in FIG. 5) so as to provide uniform heating of the entire effective length 43 of the mold 19 for both blowing and heat-setting.

The balloon may be formed of any material, preferably, compliant material, including thermoplastic and thermoset polymers. The presently preferred compliant polymeric materials include polyurethanes such as TECOTHANE from Thermedics. TECOTHANE is a thermoplastic, aromatic, polyether polyurethane synthesized from methylene disocyanate (MDI), polytetramethylene ether glycol (PTMEG) and 1,4 butanediol chain extender. TECOTHANE grade 1065D is presently preferred, and has a Shore durometer of 65D, an elongation at break of about 300%, and a high tensile strength at yield of about 10,000 psi. However, other suitable grades may be used, including TECOTHANE 1075D, having a Shore D of 75. Balloons produced from the TECOTHANE materials are particularly preferred because the axial growth of the balloon during inflation is minimized, and the axial and radial size of the balloon deflates to the original preinflation size following inflation and deflation of the balloon. Thus, inflation produces little or no axial or radial growth, so that the deflated balloons elastically recoil to the preinflation size. Other suitable compliant polymeric materials which deflate so that at least the radial size of the balloon returns to the original preinflation radial size, and which therefore have a substantially elastic recoil after deflation, include ENGAGE from DuPont Dow Elastomers (an ethylene alpha-olefin polymer) and EXACT, available from Exxon Chemical, both of which are thermoplastic polymers and are believed to be polyolefin elastomers produced from metallocene catalysts. Other suitable compliant materials include, but are not limited to, elastomeric silicones, latexes, and urethanes. The type of compliant material may be chosen to provide compatibility with the catheter shaft material, to thereby facilitate bonding of the balloon to the catheter.

The compliant material may be cross linked or uncrosslinked, depending upon the balloon material and characteristics required for a particular application. The presently preferred polyurethane balloon materials are not crosslinked. However, other suitable materials, such as the polyolefinic polymers ENGAGE and EXACT, are preferably crosslinked. By crosslinking the balloon compliant material, the final inflated balloon size can be controlled. Conventional crosslinking techniques can be used including thermal treatment and E-beam exposure. After crosslinking, initial pressurization, expansion, and preshrinking, the balloon will thereafter expand in a controlled manner to a reproducible diameter in response to a given inflation pressure, and thereby avoid overexpanding the stent (when used in a stent delivery system) to an undesirably large diameter.

The length of the compliant balloon may be about 0.8 cm to about 8 cm, preferably about 1.5 cm to about 3.0 cm; and is typically about 2.0 cm. The wall thickness is generally about 0.004 in (0.1 mm) to about 0.016 in (0.4 mm), and is typically about 0.008 in (0.2 mm). In an expanded state, the balloon diameter is generally about 0.06 in (1.5 mm) to about 0.22 in (5.5 mm), and the wall thickness is about 0.0005 in (0.012 mm) to about 0.0025 in (0.06 mm).

While particular forms of the invention have been illustrated and described, it will be apparent that various modifications can be made, without departing from the spirit and scope of the invention. Accordingly, it is not intended that the invention be limited, except as by the appended claims.

What is claimed is:

1. A method of forming a balloon, comprising:
    a. disposing a polymeric tubular product having an effective length with first and second ends within a mold;
    b. applying internal pressure to the tubular product;
    c. heating at least a portion of the tubular product to a first elevated temperature for a first predetermined period of time to form the tubular product into a balloon;
    d. maintaining the temperature of the balloon along its length to a minimal temperature differential from the first temperature;
    e. heating the balloon to a second elevated temperature for a second predetermined period of time to heat set the formed balloon; and
    cooling the balloon.
2. The method of claim 1 wherein the temperature differential is less than about 100° C.
3. The method of claim 1 wherein the temperature differential is less than about 50° C.
4. The method of claim 1 wherein the temperature differential is less than about 20° C.
5. The method of claim 1 wherein the first elevated temperature is greater than the glass transition temperature of the polymeric material forming the tubular product.
6. The method of claim 5 wherein the first elevated temperature is at least 10° C. greater than the glass transition temperature of the polymeric material forming the tubular product.
7. The method of claim 6 wherein the first elevated temperature is at least 20° C. greater than the glass transition temperature of the polymeric material forming the tubular product.
8. The method of claim 7 wherein the first elevated temperature is at least 40° C. greater than the glass transition temperature of the polymeric material forming the tubular product.
9. The method of claim 5 wherein the first elevated temperature is less than the melting temperature of the polymeric material forming the tubular product.
10. The method of claim 1 wherein the second elevated temperature is substantially equal to the first elevated temperature.
11. The method of claim 1 wherein the second elevated temperature is greater than the first elevated temperature.
12. The method of claim 11 wherein the second elevated temperature is sufficiently high to thermoset the polymeric material forming the tubular product.
13. A method of forming a balloon, comprising:
    a. disposing a polymeric tubular product having an effective length with first and second ends within a mold;
    b. applying internal pressure to the tubular product;
    c. heating at least a portion of the tubular product to a first elevated temperature for a first predetermined period of time to form the tubular product into a balloon;
    d. heating the balloon uniformly between the first and second ends to a second elevated temperature for a second predetermined period of time to heat set the formed balloon, wherein the temperature difference between the first and second ends is less than 30° C.; and
    e. cooling the balloon to substantially ambient temperature.
14. The method of claim 13 wherein the tubular product temperature difference between the first and second ends is less than about 15° C.
15. The method of claim 14 wherein the tubular product temperature difference between the first and second ends is less than about 10° C.
16. A method for forming a balloon; comprising:
    a. disposing a polymeric tubular product having an effective length with first and second ends within a mold;

b. applying internal pressure to the tubular product;

c. heating at least a portion of the tubular product to a first elevated temperature with a first heating member for a predetermined period of time to form the tubular product into a balloon;

d. heating the tubular product to a second elevated temperature with a second heating member; and e. cooling the balloon to substantially ambient temperature.

17. The method of claim 16 wherein the first heating member applies heat to the tubular product as it traverses from one end of the tubular product to the other end.

18. The method of claim 16 wherein the first heating member has an effective length at least substantially the same as the effective length of the tubular product.

19. The method of claim 18 wherein the first heating member applies heat to the tubular product simultaneously across the effective length of the tubular product.

20. The method of claim 16 wherein the second heating member applies heat to the tubular product as it traverses from one end of the tubular product to the other end.

21. The method of claim 16 wherein the second heating member applies heat to the tubular product simultaneously across the effective length of the tubular product.

22. The method of claim 16 wherein the first heating member and the second heating member are integral with one another.

23. The method of claim 16 wherein the first heating member and the second heating member are on different heating heads.

24. The method of claim 16 wherein the second elevated temperature is different from the first elevated temperature.

* * * * *

UNITED STATES PATENT AND TRADEMARK OFFICE
CERTIFICATE OF CORRECTION

PATENT NO. : 6,572,813 B1 Page 1 of 1
DATED : June 3, 2003
INVENTOR(S) : Michael Y. Zhang et al.

It is certified that error appears in the above-identified patent and that said Letters Patent is hereby corrected as shown below:

Column 8,
Line 10, before "cooling", add -- f. --.

Signed and Sealed this

Twenty-third Day of December, 2003

JAMES E. ROGAN
*Director of the United States Patent and Trademark Office*